United States Patent [19]
Peters

[11] Patent Number: 5,753,246
[45] Date of Patent: May 19, 1998

[54] PACKAGED GERMICIDAL TOWELETTE, SANITATION KIT AND METHOD FOR PROMOTING HYGIENE

[76] Inventor: Marlin W. Peters, P.O. Box 1872, Upper Marlboro, Md. 20773

[21] Appl. No.: 759,004

[22] Filed: Dec. 2, 1996

Related U.S. Application Data

[63] Continuation-in-part of Ser. No. 519,780, Nov. 20, 1995, abandoned.

[51] Int. Cl.$^6$ .................................................. A01N 25/34
[52] U.S. Cl. ........................ 424/404; 424/402; 206/581
[58] Field of Search ........................... 424/401, 402, 424/404, 405, 443, 661, 665; 221/59; 206/233, 484, 494, 812, 581

[56] References Cited

U.S. PATENT DOCUMENTS

| | | | |
|---|---|---|---|
| 2,402,982 | 7/1946 | Steenbergen | 206/63.2 R |
| 2,699,779 | 1/1955 | Lustig | 128/268 |
| 2,999,265 | 9/1961 | Duane et al. | 15/506 |
| 3,129,811 | 4/1964 | Williams | 206/46 |
| 3,150,049 | 9/1964 | Emory | 167/90 |
| 3,240,326 | 3/1966 | Miller | 206/46 |
| 3,685,645 | 8/1972 | Kawaguchi | 206/63.2 R |
| 3,783,869 | 1/1974 | Schnipper | 128/261 |
| 3,946,035 | 3/1976 | Jacquet et al. | 260/243 A |
| 4,170,325 | 10/1979 | Pawlowski et al. | 229/17 B |
| 4,220,244 | 9/1980 | Elmore | 206/210 |
| 4,307,717 | 12/1981 | Hymes et al. | 128/156 |
| 4,343,403 | 8/1982 | Daniels et al. | 206/812 |
| 4,372,447 | 2/1983 | Miller | 206/812 |
| 4,749,080 | 6/1988 | Toohey | 206/210 |
| 4,788,060 | 11/1988 | Endicott et al. | 424/443 |
| 4,896,768 | 1/1990 | Anderson | 206/210 |
| 4,981,678 | 1/1991 | Tomlinson | 424/45 |
| 4,998,984 | 3/1991 | McClendon | 206/205 |
| 5,049,440 | 9/1991 | Bornhoeft, III et al. | 428/288 |
| 5,420,350 | 5/1995 | Nishihara et al. | 564/235 |
| 5,443,385 | 8/1995 | Overmyer | 433/104 |

FOREIGN PATENT DOCUMENTS

| | | |
|---|---|---|
| 2 647 091 | 11/1990 | France . |
| 27 17 128 | 11/1978 | Germany . |
| 27 24 305 | 12/1978 | Germany . |
| 27 37 425 | 1/1979 | Germany . |
| 35 08 445 | 9/1986 | Germany . |

OTHER PUBLICATIONS

Physician's Desk Reference, 1996, Hibistat Towelette germicidal handwipe (chlorhexidine gluconate), Product Information, pp. 2841–2842, p. 342 (photo).

Primary Examiner—Thurman K. Page
Assistant Examiner—K. Shelburne
Attorney, Agent, or Firm—Richard C. Litman

[57] ABSTRACT

A sanitation kit having a packaged germicidal towelette for single-use wiping of the hands of a user, the germicide being a chlorhexidine alcohol solution for providing broad-spectrum disinfecting activity to the towelette. Aloe vera and cocoa butter are each impregnated in the towelette in an amount sufficient to counter the drying effect of the chlorhexidine alcohol solution and to provide skin-moisturizing. The towelette is hermetically sealed in a tear-open packet. A dispenser for self-serve and individual dispensing of each of said hermetically sealed envelopes is provided in various embodiments. The preferred embodiment combines the dispenser with a disposable waste container for sanitarily receiving a used towelette.

12 Claims, 3 Drawing Sheets

PACKAGED GERMICIDAL TOWELETTE, SANITATION KIT AND METHOD FOR PROMOTING HYGIENE

CROSS-REFERENCE TO RELATED APPLICATION

This application is a continuation-in-part of application Ser. No. 08/519,780, filed Nov. 20, 1995, now abandoned.

BACKGROUND OF THE INVENTION

1. Field of the Invention

The present invention relates to disposable germicidal towelettes packaged for single use, more particularly, a liquid impermeable package containing a folded anti-septic towelette treated with alcohol chlorhexidine solution, aloe vera gel and cocoa butter for use as a moisturizing, disinfectant hand-wipe.

2. Description of the Prior Art

Most people are trained from childhood onward to wash one's hands before eating and that to develop such habit is a healthful hygiene habit. Nevertheless, as adults become more rushed for time in day to day activities, such habits are generally discarded as unimportant. Yet disease consciousness is renewing with the arrival of killer viruses and other contagions, because of the rising health stakes associated with unconcerned hygiene behavior.

Even in the absence of killer viruses, the World Health Organization estimates that each year millions of people die from bacteria related diseases alone. Therefore, to minimize the risk of exposure to the germs encountered continuously in day to day activities (of which encounters most are unaware), a solution is proposed which incorporates the use of a disposable germicidal towelette packaged for single use, particularly for use where public handwash basins in commercial eating establishments are limited or unavailable, and where the risk of ingesting harmful bacterial agents are greatest. A liquid impermeable package containing a folded anti-septic towelette treated with alcohol chlorhexidine solution, aloe vera gel and cocoa butter for use as a moisturizing, disinfectant hand-wipe is suggested.

The use of chlorhexidine alcohol is well known in the art as a broad spectrum germicidal composition, usually used as a germicidal hand rinse which provides rapid bactericidal action and has a persistent antimicrobial effect. A relevant use as a towelette is described in the Physician's Desk Reference, 1996 edition, in the Product Information section at pages 2841-42, and shown packaged as individually dispensable packages at page 342. The towelette is commercially available as Hibistat® towelette germicidal handwipe (chlorhexidine gluconate with inactive ingredients including emollients, isopropyl alcohol 70% and purified water). The towelette is indicated for use where hands are physically clean, but in need of degerming, when routine handwashing is not convenient or desirable, or where no sinks are available. However, the Hibistat towelette is specifically directed for use in the medical field and fails to provide a means of effectively dispensing the towelette at eating facilities.

In U.S. Pat. No. 4,981,678 to Tomlinson, a foamable biocide composition is described containing alcoholic chlorhexidine including emollients of lanolin and polyols such as glycerol, propylene glycerol, sorbitol and low molecular weight polymers thereof, vinyl alcohols, and polyvinyl pyrollidone. No reference to the use of cocoa butter and aloe vera are noted as skin moisturizers. U.S. Pat. No. 5,049,440 to Bornhoeft, III et al. describes an antimicrobial wipe with salt and organic acid solution including aloe vera as a skin moisturizer.

The following listed patents further illustrate less relevant pre-packaged sheet materials saturated with medicaments: U.S. Pat. No. 2,402,982 to Steenbergen (bandage in petrolatum); U.S. Pat. No. 2,699,779 to Lustig (wicking wet dressing for wound); U.S. Pat. No. 2,999,265 to Duane et al. (hermetically sealed pad impregnated with epidermal bacteriostatic agent, humectant and emollient (lanolin and derivatives, non-rancidifying fatty acid, or aliphatic fatty alcohol) for use during bidet cleansing); U.S. Pat. No. 3,129,811 to Williams (liquid impregnated rolled applicator with drying agent, ethyl alcohol and fragrances); U.S. Pat. No. 3,150,049 to Emory (bath oil impregnated pad); U.S. Pat. No. 3,240,326 to Miller (germicidal impregnated pad of tissue paper for disinfecting toilet seats); U.S. Pat. No. 3,685,645 to Kawaguchi (defibrillation electrode pad); U.S. Pat. No. 3,783,869 to Schnipper (medicated sanitary napkin); U.S. Pat. No. 4,220,244 to Elmore (mirror-foiled packet and salt-water saturated face cloth); U.S. Pat. No. 4,343,403 to Daniels et al. (polyvinyl alcohol web for use as a wet towelette); U.S. Pat. No. 4,307,717 to Hymes et al. (povidone-iodine, fragrance, anti-inflammatory agent in a sterile bandage); U.S. Pat. No. 4,372,447 to Miller (polyvinyl alcohol flushable towelette); U.S. Pat. No. 4,749,080 to Toohey (terry cotton towelette) ; U.S. Pat. No. 4,788,060 to Endicott et al. (electrolyte douche and wipe composition); U.S. Pat. No. 4,896,768 to Anderson (glutaraldehyde saturated wipe pad); U.S. Pat. No. 4,998,984 to McClendon (broad spectrum anti-HIV germicidal pad); German Offenlegungsschrift No. 35 08 445 published Sep. 3, 1986 (package with impregnated cleaning layer); German Offenlegungsschrift No. 27 17 128 published Nov. 2, 1978 (freshening pack); German Offenlegungsschrift No. 27 24 305 published Dec. 7, 1978 (hygienic and abrasive pack); German Offenlegungsschrift No. 27 37 425 published Jan. 1, 1979 (paper towel with soap layer); and, French Demande de Brevet D'Invention No. 2 647 091 published Nov. 23, 1990 (biodegradable disinfectant wipe).

Other patents of interest include U.S. Pat. No. 3,946,035 to Jacquet et al. (anti-inflammatory polymeric compound) and U.S. Pat. No. 5,443,385 to Overmyer (method of disinfecting and lubricating dental device).

Although the use of chlorhexidine alcohol solution is well known as a bactericidal agent, a need still exists for means and a method to increase hygiene where a high likelihood of encounter with bacteria exists, such as at restaurants. None of the above inventions and patents, taken either singly or in combination, is seen to describe the instant invention as claimed.

SUMMARY OF THE INVENTION

Accordingly, it is a principal object of the invention to provide a sanitation kit for providing a towelette readily dispensed as a single package and which is used in lieu of hand-washing where cleansing facilities are inconvenient or unavailable and a disposal container for the used towelette.

It is another object of the invention to provide a germicidal packaged towelette having a broad-spectrum germicidal agent and packaged in a hermetically sealed storage envelope for convenient use.

It is a further object of the invention to provide a method of promoting hygiene wherein the towelettes are made readily available at locations where comestibles are consumed on-site.

Still another object of the invention is to provide a unitary dispenser, waste container and packaged towelettes for use in promoting hygiene.

It is an object of the invention to provide improved elements and arrangements thereof in an apparatus for the purposes described which is inexpensive, dependable and fully effective in accomplishing its intended purposes.

A sanitation kit is proposed having a packaged germicidal towelette for single-use wiping of the hands of a user, the germicide being a chlorhexidine alcohol solution for providing broad-spectrum disinfecting activity to the towelette. Aloe vera and cocoa butter are each impregnated in the towelette in an amount sufficient to counter the drying effect of the chlorhexidine alcohol solution and to provide skin-moisturizing. The towelette is hermetically sealed in a tear-open packet. A dispenser for self-serve and individual dispensing of each of said hermetically sealed envelopes is provided in various embodiments. The preferred embodiment combines the dispenser with a disposable waste container for sanitarily receiving a used towelette.

The above noted and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The present invention relates to disposable germicidal towelettes packaged for single use, more particularly, a liquid impermeable package containing a folded anti-septic towelette treated with alcohol chlorhexidine solution, aloe vera gel and cocoa butter for use as a moisturizing, disinfectant hand-wipe.

The packaged germicidal towelette includes a disposable, absorbent, sheet material suitable in size and strength for single-use wiping of the hands of a user and impregnated with a chlorhexidine alcohol solution. Chlorhexidine gluconate in an alcohol solution is chosen as a broad-spectrum disinfecting agent, imparted to the sheet material to create an effective anti-bacterial towelette for use against commonly encountered bacteria. A suitable size of the towelette is approximately 7 inches by 10 inches, which is large enough to provide adequate surface area for wiping the hands. A suitable web fabric as known in the prior art may be used, such as commonly used for the Wet-nap™ towelette.

To counter the drying effect of the alcohol on skin, skin moisturizers consisting of the group of aloe vera and cocoa butter are further impregnated in the sheet material. However, because one of the intended purposes of the towelette is directed towards use of the towelette immediately before eating to prevent the ingestion of bacteria from hand-borne germs, the amount of aloe vera and cocoa butter need only be sufficient to counter the drying effect of the chlorhexidine alcohol solution. For example, an excessive amount of cocoa butter may be undesirable as it may interfere with enjoyment of the meal by imparting an oily film or undesirable aroma inconsistent with the food about to be eaten. A fragrance may be impregnated into the sheet material also.

Figure 1:
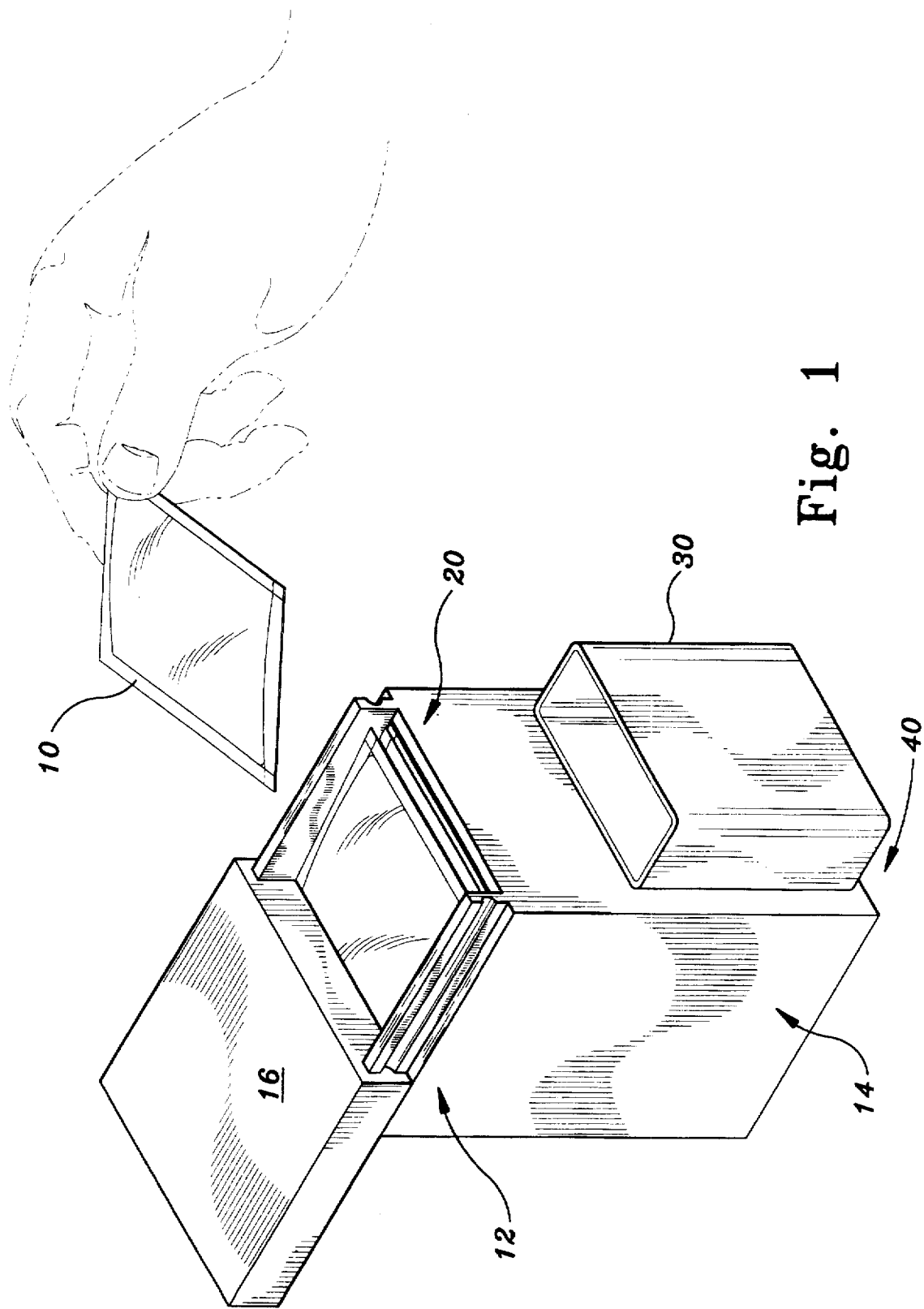
FIG. 1 is an environmental view of the germicidal towelette of present invention and a first embodiment of the sanitation kit of present invention, a free standing unit.

For convenience of the consumer, the towelette is provided in a hermetically sealed envelope 10, as suggested by FIG. 1. The hermetically sealed envelope is preferably a tear-open, rectangular packet, of pocket-sized dimensions, approximately 4 inches by 3 inches. A foil based or plasticized material may be suitable to provide a liquid and air impermeable packet. Before sealing the envelope, the sheet material is multiply folded into a generally rectangular folded form and hermetically sealed in the folded form. The towelette of the preferred 7×10 inch dimensions is able to be folded by four fold lines into a rectangular folded form measuring approximately 2.5 inches by 3.5 inches which is closely received by the envelope.

The packaged towelette may now be most effectively distributed to promote good hygiene habits by incorporating it into a sanitation kit used at a location proximate to on-site consumption of comestibles, such as bathrooms, restrooms and washrooms of restaurants and hotels. Other environments where food is sold, such as ballparks, concession stands, and the like, are particularly suited to the present invention in so far as wash basins or cleansing facilities are not commonly present or readily available. Even where such facilities are present, lines or crowds may prevent effective use of the facilities or cause unsanitary conditions.

By hermetically sealing a germicidal towelette in a single-use, tearable envelope and printing instructions for hygienic use on the envelope, the plurality of envelopes can be packaged into a dispenser for dispensing single envelopes. The packaging the envelopes may comprise stacking each package into a dispenser combined with a disposable waste disposal bin. The dispenser, either individually or in combination with the waste disposal bin, is placed in a location proximate to on-site consumption of comestibles as previously described. The dispenser may be also mounted proximate to a wash basin.

Figure 2:
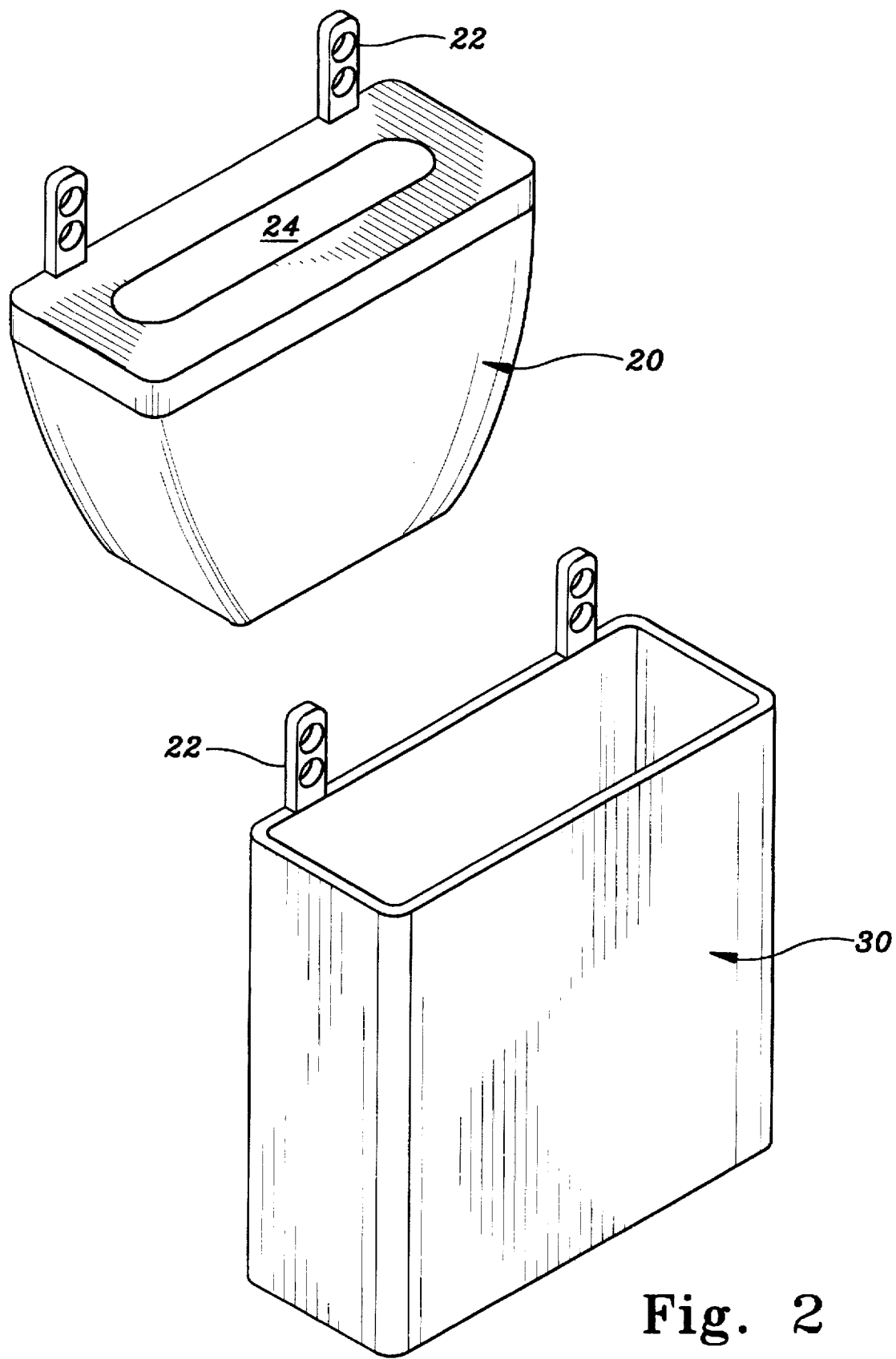
FIG. 2 is a perspective view of a second embodiment of the sanitation kit of the present invention, a wall mounted assembly.
Figure 3:
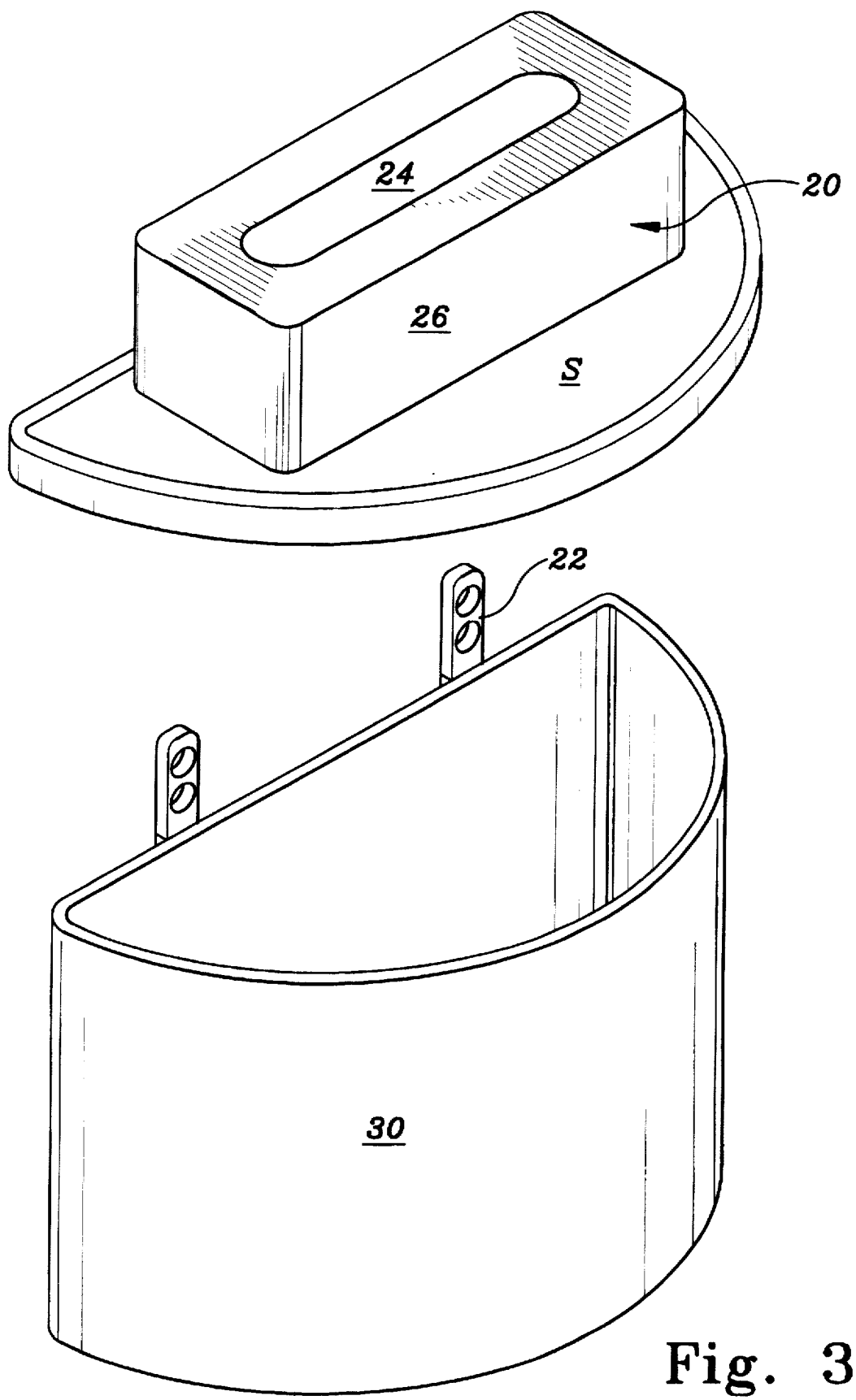
FIG. 3 is a perspective view of a third embodiment of the sanitation kit of the present invention, a shelf unit and a wall mounted waste container.

To facilitate the use of the towelette, a dispenser for self-serve and individual dispensing of each of said hermetically sealed envelopes is provided, as shown in various embodiments of FIGS. 1, 2 and 3. FIG. 1 shows a sanitation kit wherein a dispenser 20 and a waste container 30 are combined and configured as a free standing unit 40. The unit 40 has an upper portion 12 with a removable top 16. A base 14 for supports the dispenser 20 on the upper portion 12. The waste container 30 is removably attached to the base 14 by suitable attachment means, such as a hook and loop type fastener. In the alternative, the entire unit 40 may be made of inexpensive materials, such as plastics, so that the unit may be disposed of when empty.

In contrast, FIG. 2 shows a second embodiment of the sanitation kit wherein the dispenser 20 has mounting brackets 22 for hanging the dispenser on a wall. The dispenser 20 defines a slot 24 and has an internally disposed, spring-loaded mechanism (not shown) for dispensing each of the hermetically sealed envelopes through the slot 24. The waste container 30 is shown having similar mounting brackets 22 and is a separate unit into which disposable trash bags may be placed for sanitary disposal of used towelettes.

Turning now to FIG. 3, a third embodiment of the sanitation kit is shown wherein the dispenser 20 is a housing 26 for dispensing the towelettes from a convenient horizontal location, such as a shelf or counter S. The dispenser 20 also defines a slot 24 and has an internally disposed, spring-loaded mechanism (not shown) for dispensing each of the hermetically sealed envelopes through the slot 24. The waste container 30 is shown having the mounting brackets 22 and is a separate unit into which disposable trash bags may be placed for sanitary disposal of used towelettes.

It is to be understood that the present invention is not limited to the sole embodiment described above, but encompasses any and all embodiments within the scope of the following claims.

I claim:

1. A packaged germicidal towelette comprising:
    a disposable, absorbent, sheet material suitable in size and strength for single-use wiping of the hands of a user;
    a chlorhexidine alcohol solution impregnated in said disposable, absorbent sheet material for providing broad-spectrum disinfecting activity to said sheet material;
    aloe vera and cocoa butter, each impregnated in said absorbent sheet material in an amount sufficient to counter the drying effect of the chlorhexidine alcohol solution and to provide skin-moisturizing; and,
    a hermetically sealed envelope retaining said disposable, absorbent sheet-material.

2. A packaged germicidal towelette according to claim 1, wherein said hermetically sealed envelope is a tear-open packet.

3. A packaged germicidal towelette according to claim 1, wherein said disposable, absorbent sheet material is multiply folded into a folded form and hermetically sealed in said folded form in said hermetically sealed envelope being a tear-open packet.

4. The packaged germicidal towelette according to claim 1, further comprising a fragrance impregnated in said disposable, absorbent sheet material.

5. A sanitation kit, comprising:
    a packaged germicidal towelette comprising:
        a disposable, absorbent, sheet material suitable in size and strength for single-use wiping of the hands of a user;
        a chlorhexidine alcohol solution impregnated in said disposable, absorbent sheet material for providing broad-spectrum disinfecting activity to said sheet material;
        aloe vera and cocoa butter, each impregnated in said absorbent sheet material in an amount sufficient to counter the drying effect of the chlorhexidine alcohol solution and to provide skin-moisturizing; and,
    a hermetically sealed envelope retaining said disposable, absorbent sheet material, wherein said hermetically sealed envelope is a tear-open packet and wherein said disposable, absorbent sheet material is multiply folded into a folded form and hermetically sealed in said folded form in said hermetically sealed envelope;
    a dispenser for self-serve and individual dispensing of each of said hermetically sealed envelopes; and,
    a disposable waste container for sanitarily receiving a used disposable, absorbent sheet material.

6. The sanitation kit, according to claim 5 wherein said dispenser and said waste container are combined and configured as a free standing unit having an upper portion and a base for supporting the dispenser on the upper portion, and wherein further the waste container is removably attached to said base.

7. The sanitation kit, according to claim 5 wherein said dispenser has mounting brackets for hanging said dispenser on a wall.

8. The sanitation kit, according to claim 5 wherein said dispenser defines a slot and has a spring-loaded mechanism for dispensing each said hermetically sealed envelope through said slot.

9. The sanitation kit according to claim 5, wherein said packaged germicidal towelette further comprises a fragrance impregnated in said disposable, absorbent sheet material.

10. A method for promoting hygiene, comprising the steps of:
    hermetically sealing a germicidal towelette in a single use, tearable envelope;
    printing instructions for hygienic use on the envelope;
    packaging a plurality of envelopes into a dispenser for singly dispensing each envelope individually; and,
    placing the dispenser in a location proximate to on-site consumption of comestibles.

11. The method for promoting hygiene according to claim 10, wherein the step of placing the dispenser comprises mounting the dispenser proximate to a wash basin.

12. The method for promoting hygiene according to claim 10, wherein the step of packaging the envelopes comprises stacking each package into a dispenser combined with a disposable waste disposal bin.

* * * * *